(12) United States Patent
Czuppon et al.

(10) Patent No.: US 7,368,583 B2
(45) Date of Patent: May 6, 2008

(54) PROCESS FOR RECOVERY OF PLANT STEROLS FROM BY-PRODUCT OF VEGETABLE OIL REFINING

(75) Inventors: Tibor Czuppon, Budapest (HU); Zsolt Kemeny, Budapest (HU); Endrene Kovari, Budapest (HU); Katalin Recseg, Budapest (HU)

(73) Assignee: Bunge Zrt., Budapest (HU)

( * ) Notice: Subject to any disclaimer, the term of this patent is extended or adjusted under 35 U.S.C. 154(b) by 320 days.

(21) Appl. No.: 10/519,769

(22) PCT Filed: Jul. 2, 2002

(86) PCT No.: PCT/HU02/00062

§ 371 (c)(1),
(2), (4) Date: Jun. 24, 2005

(87) PCT Pub. No.: WO04/000979

PCT Pub. Date: Dec. 31, 2003

(65) Prior Publication Data

US 2006/0135794 A1 Jun. 22, 2006

(30) Foreign Application Priority Data

Jun. 19, 2002 (HU) .................................. 0202024

(51) Int. Cl.
*C07D 311/74* (2006.01)
*C07J 9/00* (2006.01)

(52) U.S. Cl. ...................................... 549/413; 552/540
(58) Field of Classification Search ................ 549/413; 552/540

See application file for complete search history.

(56) References Cited

U.S. PATENT DOCUMENTS 5,512,691 A * 4/1996 Barnicki et al. .............. 203/28
6,706,898 B2 * 3/2004 Sumner, Jr. .................. 549/413

\* cited by examiner

*Primary Examiner*—Kamal A. Saeed
(74) *Attorney, Agent, or Firm*—Jonathan Myers; Andrew Wilford

(57) ABSTRACT

The process for recovery of plant sterols and tocopherols from deodorization distillates formed during chemical or physical refining of vegetable oils consists of the following steps: free fatty acids are removed from the deodorization distillate by vacuum distillation or by continuation solvent saponification, after the removal of free fatty acids, the received material is reacted with an aromatic carboxylic acid anhydride at a temperature of 50-150° C., under reduced pressure, after the treatment with anhydride, tocopherols are removed from the mixture, and crystalline free sterols are recovered from the distillation residue containing sterol esters, di- and triglycerides by transesterification.

9 Claims, 1 Drawing Sheet

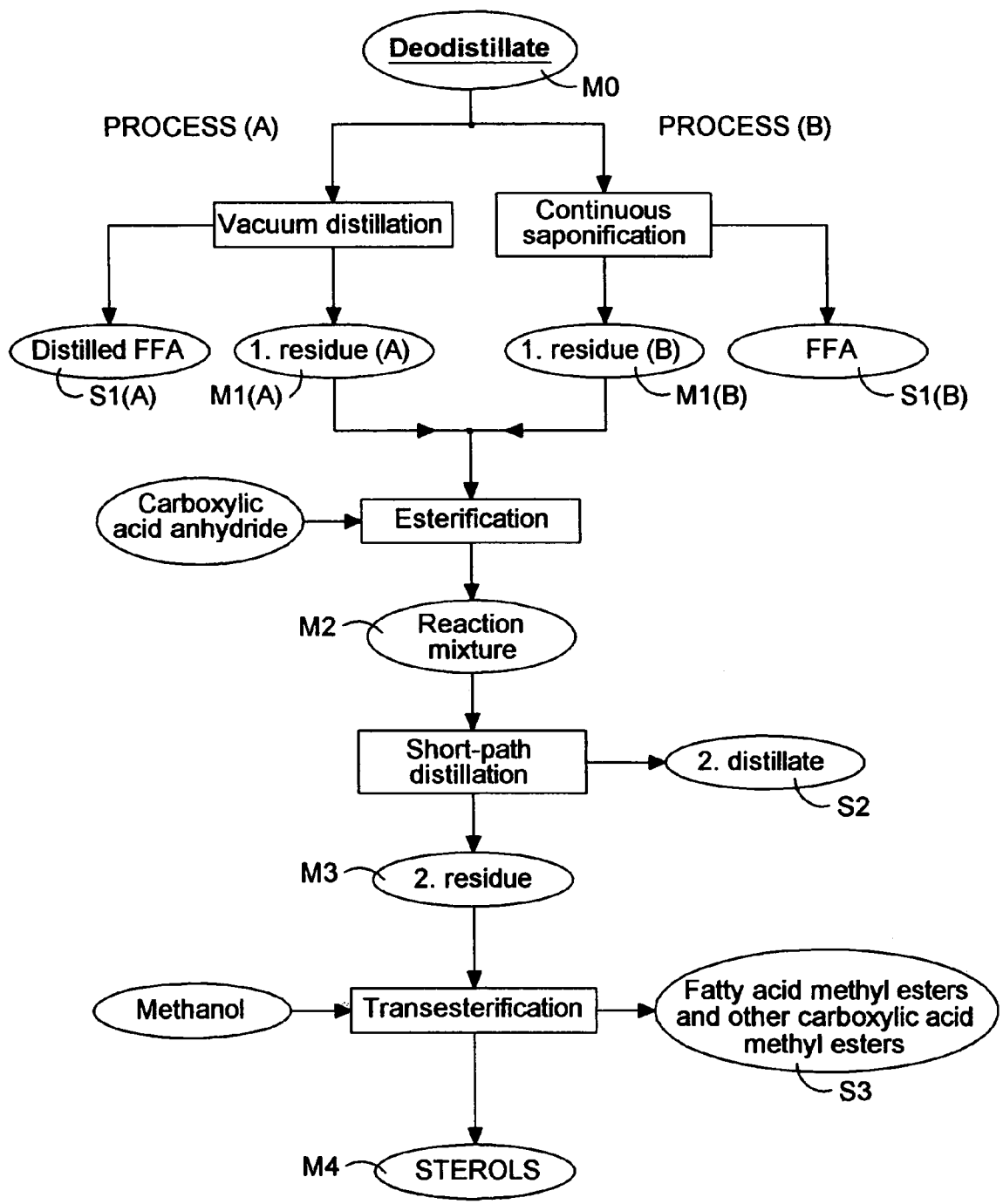

PROCESS FOR RECOVERY OF PLANT STEROLS FROM BY-PRODUCT OF VEGETABLE OIL REFINING

CROSS REFERENCE TO RELATED APPLICATIONS

This application is the US national phase of PCT application PCT/HU2002/000062 filed 2 Jul. 2002 with a claim to the priority of Hungarian patent application P0202024 itself filed 19 Jun. 2002.

FIELD OF THE INVENTION

The invention concerns the recovery of plant sterols and other valuable components such as tocopherols from a by-product of vegetable oil refining, deodorization distillate composed of sterols, sterol esters, tocopherols, fats or oils and their derivatives as well as fatty acids.

BACKGROUND OF THE INVENTION

Occurring both in plants and animals, sterols are a group of natural compounds, the most important of which are summarised in the following table:

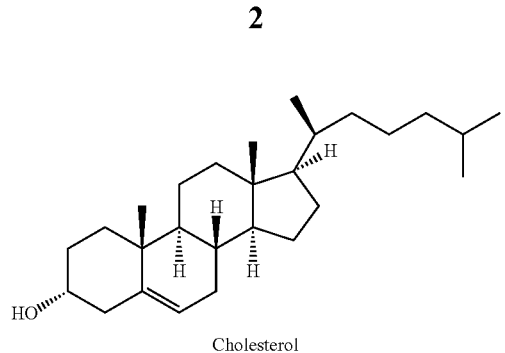

Cholesterol

Nutritional studies confirmed that plant sterols decrease the cholesterol level of the blood serum and positively influence the ratio of the LDL and HDL cholesterol level (Westrate J A, Meijer G W. Plant sterol-enriched margarines and reduction of plasma total- and LDL-cholesterol concentrations in normocholesterolaemic and mildly hypercholesterolaemic subjects. European Journal of Clinical Nutrition 1998 52: 334-43; Miettinen T A, Puska P, Gylling H, et al.

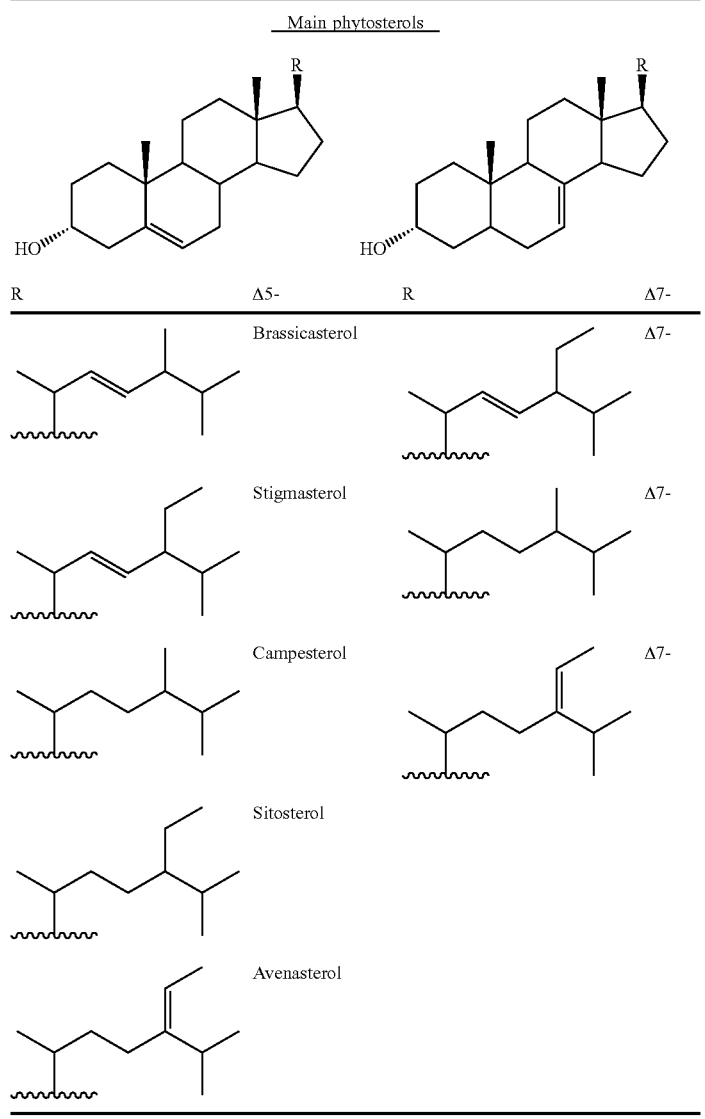

Reduction of serum cholesterol with sitostanol-ester margarine in a mildly hypercholesterolaemic population. New Engl. Journal of Medicine 1995;333:1308-1312). Plant sterols are applied predominantly in the food, pharmaceutical and cosmetic industry.

Tocopherols and tocotrienols (in general tocol compounds) possess vitamin E activity, the highest level is exhibited by α-tocopherol.

Tocopherols have important role in the human organism, due to their antioxidant properties they act as free radical scavengers and they also bind the molecular oxygen (A. Kamal-Eldin and L. A. Appleqvist: The Chemistry and Antioxidant properties of Tocopherols and Tocotrienols. *Lipids* 31. (1996) 671-701.).

The concentration of sterols and tocopherols in vegetable oils is too low to allow their industrial recovery in an economical way. At industrial scale natural sterols and tocopherols are obtained from the so-called deodorization distillate formed during refining of vegetable oils.

Vegetable oils are most widely refined by applying chemical or physical refining processes. In the last step of both processes, the oil is subjected to vacuum-steam distillation in order to remove the taste and odoriferous materials as well as the free fatty acids and also to improve the oxidative stability of the oil. Deodorization is generally performed at a temperature of 210-270° C., under reduced pressure (1-8 mbar), the deodorization distillate is obtained by condensation of the vapours formed during the operation. Besides the main components, according to their volatility various other substances appear in the deodorization distillate, the composition of which can be characterised as follows:

| free fatty acids | 30-85% |
| unsaponifiable materials | 7-35% |
| tocopherols | 1-8% |
| free sterols | 2-15% |
| sterol esters | 0-5% |
| glycerides | 5-30% |
| others | 0-5% |

* the % values relate to weight %

Numerous processes are described for recovery of sterols and tocopherols from deodorization distillates. In several patents distillation is preferably applied to remove fatty acids or fatty acid methyl esters (EP 0 333 472, U.S. Pat. Nos. 5,424,457, 5,627,289, 4,454,329). A saponification process is suggested for free fatty acid removal in the following patents: U.S. Pat. No. 3,335,154, 4,550,183 and WO 99/42471.

According to U.S. Pat. No. 5,512,691 prior to the fatty acid distillation, the free sterols are esterified with the fatty acids present in the deodorization distillate. The advantage of this step is that the boiling point range of the formed sterol esters is much higher than that of the unreacted tocopherols, which makes the separation of the two groups of compounds simple using short-path distillation.

According to U.S. Pat. No. 5,487,817 crystalline free sterols can be recovered from the sterol esters concentrated in the residue of the distillation.

Esterification of the free sterols with the free fatty acids present in the deodorization distillate requires relatively high temperature (150-250° C.), long reaction time (1-12 hours) and reduced pressure (lower than 50 mbar), in some cases application of acidic type catalyst is necessary. As a consequence of the unfavourable conditions (high temperature, long reaction time), unwanted side-reactions take place, such as degradation of tocopherols, transformation of sterols into hydrocarbons by losing the functional —OH group and a H atom as water, and increased formation of tar.

SUMMARY OF THE INVENTION

The process of the present invention for recovery of plant sterols and tocopherols from deodorization distillates formed during chemical or physical refining of vegetable oils, by distillation or saponification of the components present, can be characterised with the following steps:
i) free fatty acids are removed from the deodorization distillate by vacuum distillation or by continuous solvent saponification,
ii) after the removal of free fatty acids, the received material consisting of sterols, tocopherols, hydrocarbons, mono-, di- and triglycerides as main components is reacted with an aromatic carboxylic acid anhydride having at least 7 carbon atoms at a temperature of 50-150° C., under reduced pressure during 0.5-2 hours,
iii) after the treatment with anhydride, tocopherols are removed from the mixture applying short-path distillation,
iv) crystalline free sterols are recovered from the distillation residue containing sterol esters, di- and triglycerides by transesterification.

The raw material of the process is deodorization distillate obtained during refining of sunflower, rapeseed, soybean or corn oil, but deodorization distillates of other oils can also be applied. Free fatty acids are removed in a distillation column or in a film evaporator at 0.1-8 mbar pressure, 180-250° C. temperature.

As an alternative, free fatty acids can be saponified in an apolar/polar solvent medium at 10-40° C. during 0.5-5 minutes, applying a slight excess of lye, then the fatty acids are removed in form of soaps by separating the polar phase.

For the esterification of the deodorization distillate rid of fatty acid, we apply carboxylic acid anhydrides such as benzoic, benzyl, phenoxyacetic, phthalic, substituted phthalic acid anhydride.

The anhydrides are added in a slight excess (maximum 5 mol %) over the amount of free sterols determined by gas chromatographic analysis.

After esterification, short-path distillation of tocopherols is performed at a pressure of 0.01-0.1 bar at temperatures ranging from 200 to 260° C.

Sterols are liberated from the residue of tocopherol distillation containing 20-60 weight % sterol esters, using transesterification in methanol medium preferably in presence of sodium methylate catalyst.

During transesterification of sterol esters, the distillation residue containing sterol esters is preferably introduced continuously to the boiling sodium methylate solution and the reaction is made complete within 2-4 hours.

The crystalline plant sterols obtained according to the invention are used for pharmaceutical, cosmetic or food industrial purposes. In specific cases sterols can be further purified before application.

In the process detailed in the invention, the raw material is a by-product of vegetable oil refining (deodorization) widely referred to as deodorization distillate, which can be originated from vacuum steam distillation of sunflower, rapeseed, soybean or corn oil. The deodorization distillate contains 2-15 weight % sterols and 30-85 weight % free fatty acids. When the deodorization distillate is a by-product of physical refining of vegetable oils, the free fatty acid content of the material is more than 50 weight % (typically 60-85 weight %). Removing firstly the free fatty acids from the deodorization distillate, we can decrease the quantity of the material at least by half. Consequently, we can decrease the size of the equipment necessary for the next reaction step.

The sterol fraction is predominantly composed of the following compounds: β-sitosterol, campesterol, stigmasterol, brassicasterol (only in case of rapeseed origin), and avenasterol. The free fatty acid fraction includes C14-C24 saturated and unsaturated fatty acids (among others myristic, palmitic, stearic, arachidic, behenic and lignoceric as saturated and myristoleic, palmitoleic, oleic, linoleic, linolenic, gadoleic and nervonic acid as unsaturated fatty acid). Besides the above components the deodorization distillates consist of mono-, di-, and triglycerides as well as tocopherols (1-8 weight %), tocotrienols, hydrocarbons, sterol esters and some other minor components.

The process according to the invention is demonstrated in the sole FIGURE in this application which is a flow diagram of the steps of the process to recover plant sterols from vegetable oil deodorization distillates.

The first step of the process is the removal of the major part of the free fatty acids present in the deodorization distillate (M0) in order to decrease the quantity of the reaction mixture. The concentration factor ranges between 1.5 and 5.0 depending on the free fatty acid content and distillation parameters applied. The free fatty acids, together with the low boiling components of the unsaponifiable material are distilled off in a distillation column or film evaporator at 0.1-8 mbar pressure and 180-250° C. temperature.

There is a possibility for separation of vapours by partial condensation or isolated condensation of vapours The pre-cut fraction contains the most volatile compounds, in which short chain fatty acids and fatty acid degradation products are concentrated. The main distillate fraction (S1-A) is mainly composed of different fatty acids and it contains some other compounds in small quantity (1-9 weight %) such as monoglycerides, hydrocarbons, traces of tocopherols and sterols.

The residue of free fatty acid distillation (M1-A) contains sterols, tocopherols, hydrocarbons, mono-, di-, and triglycerides as well as some other, high boiling point compounds. The degradation and evaporation loss of sterols and tocopherols is less than 1.0%.

Alternatively, the free fatty acids can be removed from the deodorizer distillate by alkali neutralization in a medium composed of polar and apolar solvents. The reaction takes place under mild conditions: low temperature (10-40° C.), short contact time with alkali (0.5-5 min), slight or no excess of alkali (0-20%).

After saponification of the fatty acids, the components of the deodorization distillate soluble in apolar solvent can be separated from the soaps by a simple decantation. Conventional fat solvents such as hexane can be applied as apolar solvent. Concerning the polar solvent, a short-chain alcohol like methanol, ethanol, propanol or isopropanol is used. The alkali (sodium or potassium hydroxide) is applied in form of a 40-300 g/l water solution.

After solvent saponification, two phases form during decantation, the apolar phase contains triglycerides and the unsaponifiable substances, the polar phase contains the dissolved soaps. Both phases have to be thoroughly washed because of the cross-solubility of the solvents. The polar phase is washed with an apolar solvent to improve the yield, the apolar phase is washed with a polar solvent to remove the residual soaps and the traces of alkali.

Finally, the solvent is evaporated from the apolar phase resulting in a product (M1-B) containing less than 0.5 weight % free fatty acid. As a consequence of the almost entire free fatty acid removal, the theoretical concentration factor of 1.5 to 5 can be reached for sterols, sterol esters and tocopherols.

Fatty acids can be recovered from the polar phase by soap splitting in miscella using a strong mineral acid such as sulphuric or hydrochloric acid at moderate pH and ambient temperature. Generally we apply sulphuric acid, the pH is adjusted to 1-5. The fatty acid phase is separated by gravity settling, then the fatty acids are washed to neutral by water, and finally the solvents are evaporated. The free fatty acid content of the resulted material (S1-B) is at least 95 weight %.

The reaction mixture free of fatty acid according to the invention (M1-A or M1-B) is treated with acid anhydrides such as benzoic, benzyl, phenoxyacetic, phthalic, substituted phthalic acid anhydride to convert the free sterols into the corresponding sterol-esters. The reaction takes place at a temperature of 50-150° C., under reduced pressure (50-100 mbar), dosing the anhydride in 0-5 weight % excess and it lasts approximately 0.5-2 hours. The reaction is followed up by gas chromatographic analysis.

The tocopherols can be easily separated from the sterol esters by distillation based on their increased volatility difference. The tocopherols are removed by distillation in a short-path (molecular) distiller (0.01-0.1 mbar; 200-245° C.) and it yields a concentrate rich in tocopherol (18-25 weight %) as distillate (S2) and a residue (M3) with high sterol-ester content (20-60 weight %).

The next step of the process said by the invention is the liberation of free sterols from the sterol esters. The residue of short-path distillation (M3) containing mostly sterol esters, di- and triglycerides, is continuously added to a solution of methanol and sodium methylate catalyst during 1-1.5 hours, while the reaction mixture is refluxing. The completion of transesterification takes 2-4 hours. Fatty acid methyl esters rise from the sterol esters present originally as fatty acid esters and from the glycerides, furthermore carboxylic acid methyl esters depending on the applied anhydride and free sterols form. At the end of the reaction the sodium methylate catalyst is neutralized by acetic acid.

After the complete liberation of sterols, the reaction mixture is cooled to room temperature (15-25° C.) meanwhile kept stirred then the formed sterol crystals are filtered off on a vacuum or pressure filter, preferably on a centrifuge. The filtered sterols have to be washed first with methanol (2-3 times) then with hexane (also 2-3 times) to get rid of coloring materials and other impurities.

With the process described in the invention, the 85 weight % purity of sterols required for application as pharmaceutical raw material can be achieved. For food purposes a sterol content higher than 98 weight % is demanded.

In case when crystalline sterols with higher purity are needed, the amount of solvent used in the individual washing steps and/or the time of soaking between the individual filtration steps should be increased. If necessary, a re-crystallization combined with activated carbon bleaching is performed. Long chain hydrocarbons (hexane and its homologues with higher molecular weight) and alcohols (n-octanol and its homologues with higher boiling point) as well as their mixtures can be applied as solvents in the re-crystallisation step.

The first mother liquid (S3) consists of predominantly fatty acid methyl esters, other acid methyl esters and the excess methanol and it contains sodium salts originated from the catalyst in smaller quantities. In order to recover the useful materials, the methanol is distilled off from the mixture, then the sodium salts and the glycerol are removed by washing with water, and finally, one obtain pure methyl esters by means of drying and vacuum distillation.

The second mother liquid contains methanol as main component, which is recovered by distillation. The third mother liquid consists of mostly hexane, which is recovered by distillation.

The white sterol crystals are dried in an appropriate dryer under a moderate vacuum (50-100 mbar) at a temperature between 60 and 120° C.

The crystalline product (M4) obtained in this way contains at least 92 weight % free sterol and it is practically free from tocopherols and solvents.

The typical composition of the crystalline sterol product obtained by this process is the following:

| | |
|---|---|
| β-Sitosterol: | 40-65% |
| Campesterol: | 10-35% |
| Stigmasterol: | 2-25% |
| Brassicasterol: | 0-25% |
| Δ5-Avenasterol: | 0-3% |
| Other sterols: | 0-9% |

* the % values relate to weight %

The advantages of the process said by the invention is summarized as follows:

It is particularly suitable to recover sterols from deodorization distillates of physical refineries, in which case the sterol content is typically lower than 4 weight % and the free fatty acid content ranges between 60 and 85 weight %. Decreasing the quantity of the reaction mixture can decrease the size of the necessary reactors. Decreasing the processing temperature facilitates the improvement of tocopherol yield, decreases the tar formation, and furthermore considerably improves the quality of the crystalline sterol end-product. The amount of solvent used in the process is also smaller. There is no need of catalyst for the esterification of sterols, the loss caused by sterol dehydration is lower by avoiding the use of high reaction temperature and high vacuum. The processing time of sterol recovery can be shortened, the high sterol concentration and the high reactivity of anhydrides compared to that of the free fatty acids makes feasible to transform the batch system into a continuous process.

The process said by the invention is further illustrated by the subsequent examples.

EXAMPLE 1

A mixed deodorizer distillate (rape and sunflower, from physical and chemical refining process) was used as starting material. The composition of the initial mixture (M0) is characterised in Table I. The analyses were performed according to the methods given below:

Tocopherols and free sterols: AOCS Ce 7-87 gas chromatographic (GC) method;
free fatty acids (FFA): ISO 660:1996 titrimetric method;
other components (sterol-esters, glycerides, squalene): custom-designed GC method (HP-1 cross-linked methylsiloxane capillary column: 30 m/0.2 mm/0.11 μm, internal standard: hexatriacontane 1 mg/ml, oven temperature program from 170 to 320° C. at 5° C./min, from 320 to 355° C. at 4° C./min, 10 min hold, injector temperature: 350° C., detector temperature: 355° C., carrier gas: hydrogen)

The process is described in FIG. 1. The deodorization distillate (1000 g of M0) was subjected to a distillation at 1 mbar and 180° C. in a film evaporator (0.075 m$^2$) equipped with a double-jacketed dosing funnel and a controlled needle valve. The operation resulted in 594 g distilled fatty acid (S1-A) and 396 g residue (M1-A). The composition of these distillation products is summarised in Table I.

TABLE I

| Material code | M0 | | S1-A | | M1-A | |
|---|---|---|---|---|---|---|
| Mass (gram) | 1000 | | 594.0 | | 396.0 | |
| Unit | %* | gram | %* | gram | %* | gram |
| Free fatty acid | 62.34 | 623.40 | 92.25 | 547.97 | 18.76 | 74.29 |
| Total tocopherol | 2.07 | 20.65 | 0.51 | 3.04 | 4.41 | 17.46 |
| Total sterol | 3.29 | 32.86 | 0.51 | 3.05 | 7.42 | 29.37 |
| Sterol esters | 2.26 | 22.60 | 0.00 | 0.00 | 5.67 | 22.45 |
| Glycerides | 19.66 | 196.60 | 0.11 | 0.65 | 48.41 | 191.70 |

*the % values relate to weight %

EXAMPLE 2

The same deodorization distillate (M0) as in Example 1 was used as starting material in the continuous solvent saponification reaction. The raw material (400 g) was dissolved in 2400 ml hexane. An alkali solution was made from 300 ml sodium hydroxide (concentration: 125 g/l), 400 ml water and 800 ml ethanol. This alkali solution was then added to the deodorization distillate—hexane solution and the mixture was intensively stirred for 5 min at room temperature. Afterwards the whole mixture was transferred into a separation funnel and it was subjected to decantation until two phases formed with sharp phase boundary (4 hours). The two phases were then separated. The upper, apolar phase contained glycerides and the unsaponifiable substances, the lower, polar phase contained the dissolved soaps.

Both phases have to be washed because of the cross-solubility of the solvents. The polar phase was washed with an apolar solvent (3×100 ml hexane) to improve the yield, the apolar phase was washed with a polar solvent (3×100 ml ethanol) to remove the residual soaps. Afterwards the polar and apolar phases were unified respectively.

The traces of alkali substances were removed from the unified polar phase by washing with 7 weight % citric acid solution (100 ml), then the traces of citric acid and the formed salts were removed by washing with distilled water (100 ml).

Finally, evaporating the solvents from the apolar phase 148 g product (M1-B) was obtained with a residual free fatty acid content lower than 0.5 weight %. The composition of the product is described in Table II.

TABLE II

| Material code | M0 | | S1-B | | M1-B | |
|---|---|---|---|---|---|---|
| Mass (gram) | 400 | | 245.4 | | 148.0 | |
| Unit | %* | gram | %* | gram | %* | gram |
| Free fatty acid | 62.34 | 249.36 | 98.74 | 242.31 | 0.49 | 0.73 |
| Total tocopherol | 2.07 | 8.26 | 0.00 | 0.00 | 5.08 | 7.52 |
| Total sterol | 3.29 | 13.14 | 0.41 | 1.01 | 7.63 | 11.29 |

TABLE II-continued

| Material code | MO | | S1-B | | M1-B | |
|---|---|---|---|---|---|---|
| Mass (gram) | 400 | | 245.4 | | 148.0 | |
| Unit | %* | gram | %* | gram | %* | gram |
| Sterol esters | 2.26 | 9.04 | 0.00 | 0.00 | 6.06 | 8.97 |
| Glycerides | 19.66 | 78.64 | 0.00 | 0.00 | 53.07 | 78.54 |

*the % values relate to weight %

EXAMPLE 3

The residue of the first distillation of deodorization distillate (250 g M1-A) was treated with 11 g benzoic acid anhydride (90%, technical, Aldrich), we obtain free sterols from the sterol esters in this way.

Firstly the distillation residue was heated to 120° C. and then, this temperature was maintained for 1 hour at 10 mbar residual pressure to remove the moisture traces. Afterwards the mixture was cooled to 80° C. and the benzoic acid anhydride was added. The esterification reaction took place at a temperature of 150° C. at 100 mbar residual pressure during 2 hours. The reaction was followed by gas chromatographic (GC) analysis. In the end, we achieved 261 g reaction mixture (M2). The composition of the product is shown in Table III.

TABLE III

| Material code | M1-A | | M2 | |
|---|---|---|---|---|
| Mass (gram) | 250.0 | | 261.0 | |
| Unit | %* | gram | %* | gram |
| Free fatty acid | 18.76 | 46.90 | 15.83 | 41.32 |
| Total tocopherol | 4.41 | 11.02 | 4.10 | 10.69 |
| Total sterol | 7.42 | 18.54 | 0.00 | 0.00 |
| Sterol esters | 5.67 | 14.18 | 22.11 | 57.71 |
| Glycerides | 48.41 | 121.03 | 47.24 | 123.30 |

*the % values relate to weight %

EXAMPLE 4

The esterified mixture (250 g M2) was treated in a short-path distiller (0.075 m²) equipped with a heated jacketed dosing funnel and a control needle valve.

The operation resulted in a second distillate (44 g S2) and a second distillation residue (199 g M3). The distillate obtained in this step is the tocopherol concentrate. The composition of the distillation products is characterized in Table IV.

TABLE IV

| Material code | M2 | | S2 | | M3 | |
|---|---|---|---|---|---|---|
| Mass (gram) | 250.0 | | 55.0 | | 191.0 | |
| Unit | %* | gram | %* | gram | %* | gram |
| Free fatty acid | 15.83 | 39.58 | 66.47 | 36.56 | 1.14 | 2.18 |
| Total tocopherol | 4.10 | 10.25 | 18.56 | 10.21 | 0.00 | 0.00 |
| Total sterol | 0.00 | 0.00 | 0.00 | 0.00 | 0.00 | 0.00 |
| Sterol esters | 22.11 | 55.28 | 0.20 | 0.11 | 28.72 | 54.86 |
| Glycerides | 47.24 | 118.10 | 9.87 | 5.43 | 58.65 | 112.02 |

*the % values relate to weight %

EXAMPLE 5

In order to transesterify the sterol esters received in the short-path distillation step, firstly a solution composed of 100 ml methanol (water content: <0.02 weight %) and 10 ml sodium methylate (30% w/w) was made, then this solution was heated to its boiling point and refluxed under stirring. The second distillation residue (100 g M3) was heated to 60° C., then it was added dropwise to the boiling sodium methylate solution during one hour. After completing the dosage, the mixture was agitated under reflux for one hour.

The reaction was followed by gas chromatographic (GC) analysis. At the end of the reaction 5 ml glacial acetic acid was added to the mixture in order to neutralize the sodium methylate catalyst. After 5 minutes agitation the mixture was cooled down to ambient temperature (20° C.). The formed crystals were filtered off and washed with methanol (3×30 ml) then with hexane (3×30 ml) until white sterol crystals were obtained.

The filtered, washed crystals were dried in a drying oven at 80° C. The composition of the 17 g crystalline sterols (M4) obtained is given in Table V.

The first mother-liquid is composed predominantly of methyl esters and the excess methanol and it contains the catalyst residues, glycerol and other contaminants in smaller quantities.

After evaporating the solvent from the mixture, 77 g of intermediate product and a mother-liquid rich in methyl esters (S3) was received, the composition of which is described in Table V.

TABLE V

| Material code | S3 | | Material code | M4 | |
|---|---|---|---|---|---|
| Mass (gram) | 77.0 | | Mass (gram) | 17.0 | |
| Unit | %* | gram | Unit | %* | gram |
| Methyl esters**: | 89.64 | 69.02 | Brassicasterol | 20.39 | 3.47 |
| Free fatty acids | 0.45 | 0.35 | Campesterol | 26.13 | 4.44 |
| Total tocopherols | 0.00 | 0.00 | Stigmasterol | 3.30 | 0.56 |
| Total sterols | 2.43 | 1.87 | β-Sitosterol | 42.92 | 7.30 |
| Sterol esters | 0.69 | 0.53 | Other sterols | 2.77 | 0.47 |
| Glycerides | 0.76 | 0.59 | Total sterols | 95.51 | 16.24 |

*the % values relate to weight %
**fatty acid- and other carboxylic acid methyl esters For further purification of methyl-esters, first the traces of the catalyst and glycerol as well as other water-soluble components were removed by washing with water, then the washed material was dried and finally, pure methyl esters were obtained by vacuum distillation.

What is claimed is:

1. A process for recovery of plant sterols and tocopherols from deodorization distillates formed during chemical or physical refining of vegetable oils, by distillation or saponification of the components present, which comprises the steps of
   i) removing free fatty acids from the deodorization distillate by vacuum distillation or by continuous solvent saponification to obtain a material comprising sterols, tocopherols, hydrocarbons, mono-, di- and triglycerides as main components,
   ii) after the removal of the free fatty acids, reacting the obtained material comprising sterols, tocopherols, hydrocarbons, mono-, di- and triglycerides as main components with an aromatic carboxylic acid anhydride having at least 7 carbon atoms at a temperature of 50-150° C., under reduced pressure over 0.5-2 hours, iii) after the treatment with anhydride, removing tocopherols from the reaction mixture of step ii) by applying short-path distillation, and iv) recovering crystalline free sterols from the distillate residue containing sterol esters, di- and triglycerides by transesterification.

2. The process according to claim 1, wherein the deodorization distillate is a deodorization distillate obtained during refining of sunflower, rapeseed, soybean and corn oil.

3. The process according to claim 1i) wherein the free fatty acids are distilled in a distillation column or in a film evaporator at a pressure of 0.1-8 mbar at temperatures ranging from 180 to 250° C.

4. The process according to claim 1i) wherein the free fatty acids are saponified in a medium of polar/apolar solvents at 10-40° C. temperature, over 0.5-5 minutes in presence of a slight excess of alkali, and the free fatty acids are removed by separating the polar phase.

5. The process according to claim 1ii) wherein a benzoic, benzyl, phenoxyacetic, phthalic, or substituted phthalic acid anhydride is applied as carboxylic acid anhydride.

6. The process according to claim 1ii) wherein the anhydrides are applied in an excess limited to 5 mol % over the amount of sterols determined by gas chromatographic analysis.

7. The process according to claim 1iii) wherein the short path distillation of tocopherols is performed at 0.01-0.1 bar pressure applying 200-260° C.

8. The process according to claim 1iv) wherein the sterols are recovered from the 20-60 weight % sterol-ester containing residue of tocopherol distillation, applying transesterification, in presence of sodium methylate catalyst.

9. The process according to claim 8 wherein during said transesterification of sterol esters, the distillation residue rich in sterol esters is added continuously to a refluxed sodium methylate solution and the reaction is made complete within 2-4 hours.

* * * * *